United States Patent [19]

Fisher et al.

[11] 4,244,376

[45] Jan. 13, 1981

[54] MEASUREMENT OF EVOKED NERVOUS SYSTEM POTENTIALS

[76] Inventors: Charles B. Fisher, 2850 Hill Park Rd., Montreal, Quebec H3H 1T1, Canada; Sidney T. Fisher, 53 Morrison Ave., Mt. Royal, Montreal, Quebec H3R 1K3, Canada

[21] Appl. No.: 119,769

[22] Filed: Feb. 8, 1980

[51] Int. Cl.³ .............................................. A61B 5/04
[52] U.S. Cl. ..................................... 128/731; 128/901
[58] Field of Search ................................ 128/731, 901

[56] References Cited

U.S. PATENT DOCUMENTS

| 3,498,288 | 3/1970 | Max et al. | 128/731 |
| 3,848,586 | 11/1974 | Suzuki et al. | 128/731 |

OTHER PUBLICATIONS

Plumb et al., "IEEE Transactions on Biomedical Engineering," vol. 11, No. 4, Oct. 1967, pp. 157–159.

Johns et al., "Electroencephalography Clinical Neurophysiology," vol. 37, No. 4, pp. 414–416, Oct. 1974.

Primary Examiner—William E. Kamm

[57] ABSTRACT

Steady-state evoked potentials from the nervous system, measured on the scalp and elsewhere on the body in response to specific periodic sensory stimuli, contain the fundamental frequency of the stimulus and other waves, and are of the order of 40 dB below potentials due to general electrical activity of the nervous system which may be considered as noise. Medical information revealed by evoked potentials is extremely valuable but is limited by measuring methods of the prior art and by the background noise. In this disclosure the periodic steady-state evoked potential from a periodic stimulus, shifted to a suitable frequency band, is sampled at instants of zero-crossings of the shifted evoked potential, at the Nyquist frequency or greater for the noise frequency band, and the resultant samples of noise are reconstructed in a filter and subtracted from the entire evoked potential, to produce as a resultant the evoked potential substantially free from background noise.

3 Claims, 2 Drawing Figures

4,244,376

MEASUREMENT OF EVOKED NERVOUS SYSTEM POTENTIALS

BACKGROUND OF THE INVENTION

This invention relates to measurement of steady-state evoked potentials from the nervous system measured on the body by means which substantially reduces background noise and does not alter the evoked potential.

Steady-state evoked potentials are caused by a rapidly repeated periodic tactile, auditory, optical or other stimulus, and are of great medical value, first to reveal specific brain activities in which different types of information are handled simultaneously in separate channels, second to provide an objective indicator of sensory function where perceptual tests are impractical, as they are with infants and animals, and third to distinguish organic from psychogenic disorders.

A serious difficulty in the use of apparatus of the prior art is to detect the relatively weak evoked potentials in the presence of much stronger background noise due to the general electrical activity of the nervous system. The measurement means of the prior art uses highly selective circuits at the fundamental frequency of the stimulas and at each higher harmonic in order to pass the evoked potential and stop background noise. This is unsatisfactory in that it restricts the response of the apparatus to a number of narrow bands, which may be narrower than the evoked potentials, on the probably erroneous assumption that the evoked potentials are simple sine functions with harmonic frequency ratios. If an evoked potential consists of two or more sine functions not harmonically related this method of measurement is inadequate and misleading. It seems probable that in many cases the stimulus in not a simple sine function, and that the prior art measurement means are largely responding to the characteristics of the stimulus. Even when the stimulas is a sine function the evoked potential may involve amplitude modulation, angle modulation, amplitude limiting and other processes that render the Fourier statement of the evoked potential, as given by measuring instruments of the prior art, incomplete and perhaps inaccurate. In addition, filters narrow enough to block substantially all noise have a very slow response. Apparatus according to this invention substantially removes all noise, from a band including at least one harmonic component of the evoked potential, without materially altering the amplitude or phase of closely associated components, such as sidebands, in the same band as a harmonic component.

We do not know of any relevant prior art.

BRIEF DESCRIPTION OF THE INVENTION

Steady-state evoked potential appears at the surface of the body in response to electrical activity of the nervous system, caused by a rapidly repeated periodic tactile, auditory, optical or other stimulus. The evoked potential is known to have a fundamental component with the same frequency as the stimulus, and may also have components at other harmonics, plus amplitude-modulation sidebands associated with the fundamental and its harmonics. The evoked potentials are low, of the order of a few microvolts, and are difficult to separate without distortion from the background noise potentials due to the general electrical activity of the nervous system, which may be 20 to 40 dB higher than the evoked potentials. The fundamental frequency of the potentials, which may be regarded as the first harmonic of the stimulus frequency, typically covers a range of 5 to 20 Hz. In the apparatus of this invention the components of the evoked potential are separately shifted by well-known modulation methods to a selected frequency band defined by a first band-pass filter, with a bandwidth less than the fundamental frequency, and which includes one harmonic component of the evoked potential plus any associated sidebands and background noise in the selected frequency band. The lowest frequency of the selected frequency band has a frequency of zero-crossings greater than the minimum sampling or Nyquist frequency for the selected frequency band.

The selected frequency band from the band-pass filter is then sampled in a sampling gate with regularly-occurring gating pulses controlled in phase and frequency by the periodic stimulus means, with a repetition frequency greater than the minimum sampling or Nyquist frequency for the selected frequency band, occurring only at instants of zero-crossings of a harmonic of the evoked potential in the selected frequency band. Thus the output of the sampling gate contains samples of the background noise but no samples of the evoked potential, and is reconstructed in analog form in a second band-pass filter with the pass-band of the selected frequency band, as a replica of the noise in the selected frequency band at the input to the sampling gate. This noise is amplified and applied to one input of a subtraction circuit. The output of the first band-pass filter is also delivered to an equalizer having attenuation and delay characteristics identical with the second band-pass filter and the following amplifier, and is delivered to a second input of the subtraction circuit. With correct amplifier gain the resultant at the output of the subtraction circuit is the frequency-shifted component of the evoked potential with any associated sidebands, substantially free from background noise. This wave may be observed, analysed, measured or recorded as appropriate, or shifted to its original position in the spectrum by well-known modulation methods.

DETAILED DESCRIPTION OF THE INVENTION

This invention is based on theorems as follows:

(1) When a continuous band-limited function occupying a selected frequency band is sampled for short periods at a frequency greater than the minimum sampling or Nyquist frequency for the selected frequency band, the Nyquist frequency being a well-known discontinuous function of the bandwidth and the highest frequency of the selected frequency band, varying between 1 and 4 bandwidths, the resultant sequence of samples fully defines the continuous band-limited function. A well-known theorem gives the range of the Nyquist function as 2 to 4, and an extension stated in U.S. Pat. No. 4,178,553 class 325/487.000 granted Dec. 11, 1979 to Fisher et al extends the range as 1 to 2 for functions which represent double-sideband amplitude-modulated waves.

(2) When the sequence of samples of paragraph (1) above is passed through a reconstruction filter with the pass-band the same as the selected frequency band an analog replica of the continuous band-limited function is reconstructed, differing from the original only by an amplitude factor and by the delay and frequency distortion of the filter. The replica is independent of the actual instants of sampling, as long as these occur regularly with greater than the minimum or Nyquist frequency. This is a well-known theorem.

(3) We have discovered an exception to the theorems of paragraphs (1) and (2) above, and this exception provides the theoretical basis of this invention. If the selected frequency band contains a periodic function, such as a sine wave or an amplitude-modulated sine wave, with regularly-occurring zero-crossings at a frequency greater than the minimum sampling or Nyquist frequency for the selected frequency band, and all instants of sampling occur at zero-crossings of the periodic function, then the resultant sequence of samples contains no components of the periodic function, and when the sampled wave is passed through a reconstruction filter with a pass-band the same as the selected frequency band, an analog replica of the continuous band-limited function is reconstructed, differing from the original only by an amplitude factor, the delay and frequency distortion of the reconstruction filter, and the substantial elimination of the periodic function. The proof of this theorem is self-evident, as the continuous band-limited function is fully defined by the samples taken at a frequency greater than its minimum sampling or Nyquist frequency, and each of the samples has been taken at an instant of zero-crossing of the periodic function. The theorem is seen to be true even when the sampling period is a substantial portion of the period of the periodic function, as long as each sampling period is centered on an instant of zero-crossing.

Figure 1:
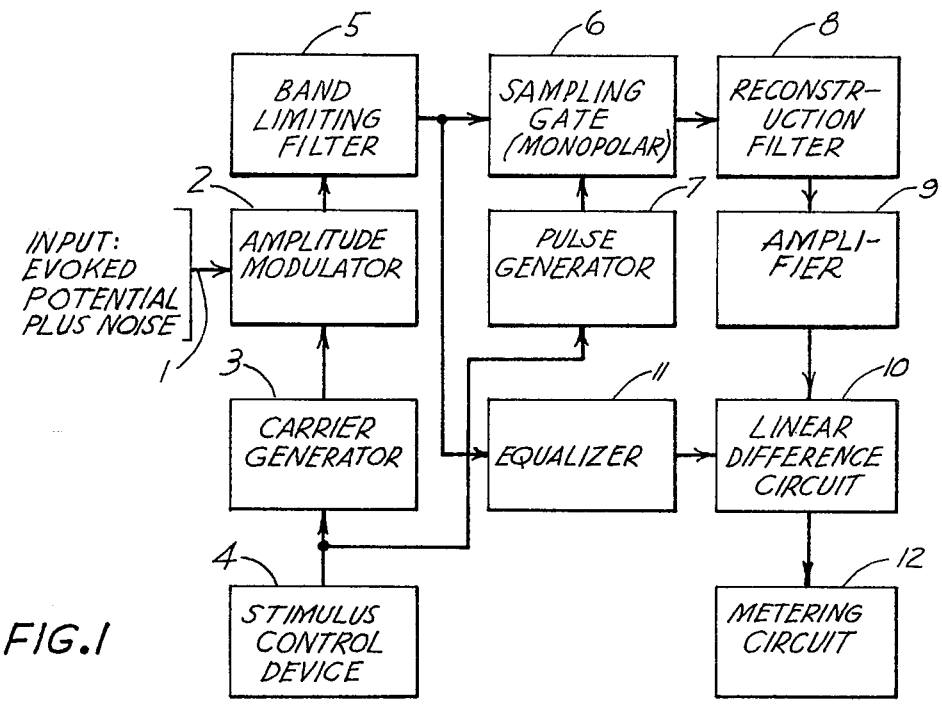
FIG. 1 shows in simplified block schematic form measuring apparatus for evoked potentials, according to this invention, using linear subtraction means.

FIG. 1 shows in simplified block schematic form measuring apparatus for evoked potentials from the nervous system according to this invention, using a linear device as the subtraction circuit.

Figure 2:
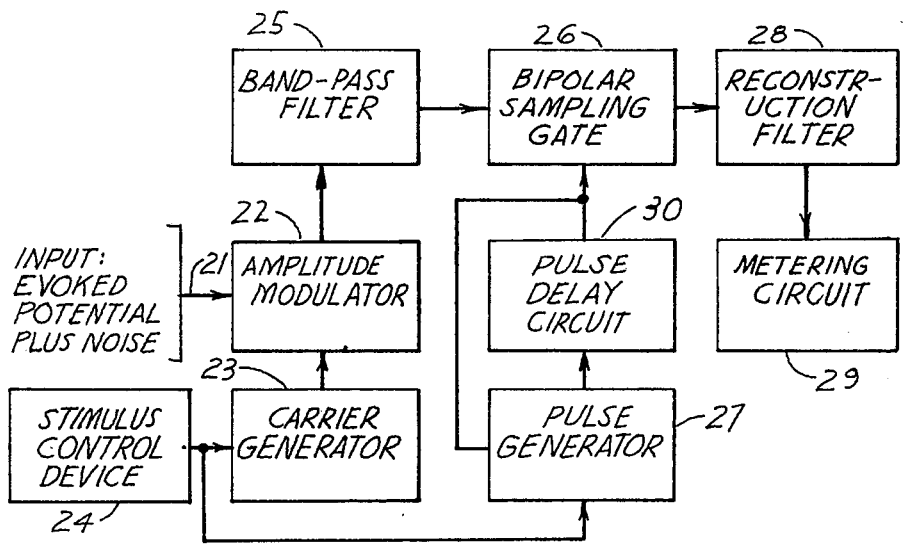
FIG. 2 shows a simplified block schematic diagram of measuring apparatus for evoked potentials, according to this invention, using a bipolar sampling gate with two spaced sequences of gating pulses as the subtraction means.

FIG. 2 shows a simplified schematic block diagram of measuring apparatus according to this invention, in which a bipolar gate with two sequences of gating pulses is the equivalent of subtraction means.

In FIG. 1 an input wave made up of an evoked potential at the first harmonic or fundamental frequency of a periodic sensory stimulus, together with other harmonic components at positive integral multiples of the stimulus frequency, plus any sidebands associated with any harmonic component due to amplitude modulation by other components evoked by the electrical activity of the nervous system, plus background noise in the band of the evoked potential due to the general electrical activity of the nervous system, appears on lead 1 and is delivered to amplitude modulator 2, supplied with a carrier wave from carrier generator 3, which is controlled in frequency and phase by an input wave from periodic sensory stimulus control device 4, which controls the frequency and timing of the periodic sensory stimulus. The input wave, shifted upwards in frequency by the carrier frequency from generator 3, is delivered to band-limiting filter 5 which has as a pass-band a selected frequency band narrower than the frequency of the periodic sensory stimulus. Carrier generator 3 is set to a frequency so that filter 5 passes one of the frequency-shifted harmonic components of the evoked potential together with any associated amplitude-modulation sidebands and background noise in the pass-band of filter 5, to sampling gate 6. Gate 6 receives regularly-occurring gating pulses from pulse generator 7, controlled in frequency and timing by periodic sensory stimulus control device 4, at a frequency greater than the minimum sampling or Nyquist frequency for the selected frequency band, each pulse at an instant of zero-crossing of the harmonic component at the input to gate 6, the pulse frequency being equal to the frequency of zero-crossings divided by a positive integer of the harmonic component.

The output of gate 6, consisting of a sequence of samples which completely defines the background noise, but is substantially free from the harmonic component and any sidebands, as present at the input to gate 6, is delivered to reconstruction filter 8, which has as a pass-band the selected frequency band, and delivers at its output a replica of the background noise in the selected frequency band in analog form, unaltered from the noise at the input to gate 6 except for an amplitude factor and delay and frequency distortion due to filter 8. The output of filter 8 is amplified by amplifier 9 in order to correct the amplitude factor and is delivered to a first input of linear difference circuit 10.

The input to gate 6 is also delivered through equalizer 11 to the second input of linear difference circuit 10. Equalizer 11 corrects the attenuation and delay over the selected frequency band from the input of gate 7 to the second input of linear difference circuit 10, so as to be identical with the attenuation and delay over the selected frequency band from the input of gate 6 to the first input of linear difference circuit 10. Thus the output of linear difference circuit 10 comprises the selected harmonic component with any associated sidebands, substantially free from background noise.

The output of linear difference circuit 10 is delivered to metering circuit 12 for observation, analysis, measurement and recording as appropriate. If desired an amplitude modulator supplied with carrier from carrier generator 3 may be provided to restore the output of linear difference circuit 10 to its position in the spectrum on lead 1 before delivery to circuit 12.

FIG. 2 shows a simplified block schematic diagram of measuring apparatus for evoked nervous system potentials, according to this invention, using a bipolar sampling gate with two spaced sequences of gating pulses as the subtraction means.

An input wave made up of an evoked potential with the fundamental or first harmonic frequency of the periodic sensory stimulus, together with the other harmonic components at positive integral multiples of the stimulus frequency, plus any sidebands associated with any harmonic component due to amplitude modulation by other components of the electrical activity of the nervous system, plus background noise in the band of the evoked potential due to the general electrical activity of the nervous system, appears as an input wave on lead 21 and is delivered to amplitude modulator 22, supplied with a carrier wave from carrier generator 23, which is controlled in frequency and phase by control waves from periodic sensory stimulus control device 24. The input wave, shifted upward in frequency by the carrier frequency from generator 23, is delivered to band-pass filter 25, which has a pass-band a selected frequency band narrower than the frequency of the periodic sensory stimulus. Carrier generator 23 is set to a frequency so that filter 25 passes one of the harmonic components of the evoked potential together with any associated amplitude-modulation sidebands and background noise in the pass-band of filter 25, to bipolar sampling gate 26. This is a well-known device which is in effect a subtraction circuit, and is the equivalent of a switch normally open, which completes the circuit from gate input to gate output with one polarity when driven by a gating pulse of one polarity, and completes the circuit with the opposite polarity when driven by a gating pulse of a second polarity. This device is widely used in single-sideband multiplex modulators and demodulators, and may consist of four diodes in a lattice connection between two center-tapped transformers.

Gate 26 receives a first sequence of regularly-occurring gating pulses of a first polarity from pulse generator 27, controlled in frequency and timing from periodic sensory control device 24, at a frequency greater than the minimum sampling or Nyquist frequency for the selected frequency band and equal to the frequency of zero-crossings of the harmonic component divided by an odd positive integer, each pulse occurring at an instant of a zero-crossing of the harmonic component at the input to gate 26. The output of gate 26, assuming the presence of only the first sequence of samples of a first polarity, completely defines the background noise but is substantially free from the harmonic component and its sidebands, as present at the input to gate 26.

The output of gate 26 that is due to the first sequence of samples is delivered to reconstruction filter 28, which has as a pass-band the selected frequency band, and produces at its output a replica of the background noise in the selected frequency band in analog form, unaltered from the noise at the input to gate 26 except for an amplitude factor and delay and frequency distortion due to filter 28.

Gate 26 receives a second sequence of gating pulses from pulse generator 27, equal in duration to the pulses of the first sequence, delayed by a period approximately equal to an odd number of quarter periods of the component, and reversed in polarity from the first pulse sequence, through pulse delay circuit 30, a device well-known in the prior art, at a frequency greater than the minimum sampling or Nyquist frequency for the selected frequency band. This produces a sequence of samples reversed in polarity, each at an instant about one-quarter of the component period from a zero-crossing of the evoked potential component. If the component is a sine wave these samples occur alternately at positive and negative peaks of the component.

The output of gate 26 therefore fully defines the evoked potential component with any sidebands and the background noise in the selected frequency band at the input to gate 26, and this second sequence of samples is delivered to reconstruction filter 28, and produces at its output a replica of the evoked potential component with any sidebands and the background noise in the selected frequency band, all in analog form with reversed polarity, unaltered from the input wave at the input to gate 26 except for an amplitude factor and delay and frequency distortion due to filter 28.

The principle of superposition clearly applies to filter 28, so that when both sequences of pulses are applied to gate 26, and thus both sequences of samples are applied to filter 28, the reconstructed background noise waves from the two sequences samples have equal and opposed amplitudes at every instant and in effect are subtracted from one another, as the reconstructed noise waves of opposite polarity cancel each other. Filter 28 delivers the reconstructed evoked potential component with any associated sidebands, substantially free from background noise, to metering circuit 29 for observation, analysis, measurement and recording as appropriate. If desired an amplitude modulator supplied with carrier from carrier generator 23 may be provided to restore the output of filter 28 to its position in the spectrum on lead 21.

We claim:

1. Measuring apparatus for an evoked nervous system potential, due to a periodic sensory stimulus, which delivers each component of said potential substantially unaltered in relative amplitude and timing, and substantially free from back-ground noise due to the general electrical activity of the nervous system, which comprises:

pick-up electrodes or equal means for obtaining said evoked nervous system potential from the surface of the body containing said nervous system, and frequency shifting means which receives and is set to shift said evoked potential by an approximate frequency which is precisely controlled by the frequency and phase of a harmonic of said periodic sensory stimulus, which shifts said evoked potential to a selected frequency band which has a bandwidth less than the frequency of said periodic sensory stimulus, the lowest frequency in said selected frequency band having a frequency of zero-crossings greater than the minimum shaping or Nyquist frequency for said selected frequency band, and band-limiting filter means which receives the output of said frequency shifting means and has a pass-band approximately the same as said selected frequency band, and pulse generating means producing a first regularly-occurring sequence of pulses of the same polarity, controlled in frequency and timing by the frequency of said periodic sensory stimulus, which occur at instants of zero-crossings of said evoked potential at the input to said sampling means, at a frequency greater than the minimum sampling or Nyquist frequency of said selected frequency band, and said sampling means which receives as input the output of said band-limiting filter means, and the output of said pulse generating means as gating pulses, and which produces samples with unchanged polarity for the first sequence of gating pulses, and filter reconstruction means with a pass-band substantially the same as said selected frequency band, which reconstructs the output of said sampling means in analog form as a replica of said background noise, and subtraction means which subtracts said replica of background noise at the output of said filter reconstruction means from the wave at the output of said band-limiting filter means so that the output from said subtraction means is said evoked potential substantially unaltered in relative phase and amplitude and substantially free from said background noise, and metering circuit means which receives the output of said subtraction means.

2. Measuring apparatus in accordance with claim 1, in which said subtraction means comprises:

amplifier means which amplifies the output of said filter reconstruction means, and equalizer means which receives the output of said band-limiting filter means and adjusts the amplitude and delay of said output so as to be equal in amplitude at every instant to the output of said amplifier means, and linear difference circuit means which receives the output of said amplifier means at a first input, and receives the output of said equalizer means at a second input, and subtracts the wave at said first input from the wave at said second input, to produce as a resultant said evoked potential substantially free from said background noise.

3. Measuring apparatus in accordance with claim 1 in which said subtraction means comprises:

pulse delay circuit means which also receives said first sequence of pulses from said pulse generating means and produces a second sequence of pulses of the same amplitude and duration as said first sequence of pulses, but reversed in polarity and delayed by an odd integral number of quarter periods of said component from said first sequence, and which delivers said second sequence of pulses to said sampling means, thus producing in the output of said sampling means a sequence of samples reversed in polarity from the first sequence of samples produced by said first sequence of pulses.

* * * * *

UNITED STATES PATENT AND TRADEMARK OFFICE
CERTIFICATE OF CORRECTION

PATENT NO. : 4,244,376
DATED : January 13, 1981
INVENTOR(S) : Charles B. Fisher and Sidney T. Fisher It is certified that error appears in the above—identified patent and that said Letters Patent is hereby corrected as shown below:

In column 1, change line 38 to read:
"...Even when the stimulus is a sine function the evoked...".

In column 4, change line 66 to read:
"...band-pass filter 25, which has as a pass-band a selected...".

In column 6, change line 30 to read:
"...ings greater than the minimum sampling or Nyquist...".

Signed and Sealed this

Second Day of June 1981

[SEAL]

Attest:

RENE D. TEGTMEYER

*Attesting Officer*     *Acting Commissioner of Patents and Trademarks*